(12) United States Patent
Persat

(10) Patent No.: US 9,066,752 B2
(45) Date of Patent: Jun. 30, 2015

(54) DEVICE FOR INJECTING A VISCOUS FLUID INTO THE BODY

(76) Inventor: Jean-Charles Persat, Collex-Bossy (CH)

( * ) Notice: Subject to any disclaimer, the term of this patent is extended or adjusted under 35 U.S.C. 154(b) by 331 days.

(21) Appl. No.: 12/935,094

(22) PCT Filed: Mar. 26, 2009

(86) PCT No.: PCT/EP2009/053632
§ 371 (c)(1),
(2), (4) Date: Sep. 28, 2010

(87) PCT Pub. No.: WO2009/118397
PCT Pub. Date: Oct. 1, 2009

(65) Prior Publication Data
US 2011/0015574 A1  Jan. 20, 2011

(30) Foreign Application Priority Data
Mar. 28, 2008 (FR) .................................. 08 52010

(51) Int. Cl.
| | |
|---|---|
| *A61M 5/315* | (2006.01) |
| *A61B 17/34* | (2006.01) |
| *A61B 17/88* | (2006.01) |
| *A61F 2/30* | (2006.01) |
| *A61F 2/46* | (2006.01) |

(52) U.S. Cl.
CPC ......... *A61B 17/3472* (2013.01); *A61B 17/8816* (2013.01); *A61B 17/8827* (2013.01); *A61B 17/8836* (2013.01); *A61F 2002/30235* (2013.01); *A61F 2002/30538* (2013.01); *A61F 2002/30601* (2013.01); *A61F 2002/4653* (2013.01); *A61F 2002/4663* (2013.01); *A61F 2002/467* (2013.01); *A61F 2230/0069* (2013.01); *A61F 2250/0006* (2013.01)

(58) Field of Classification Search
CPC ........... A61B 17/3472; A61B 17/8802; A61B 17/8805; A61B 17/8816; A61B 17/8827
USPC ............... 604/113, 264, 523, 524; 606/92–95
See application file for complete search history.

(56) References Cited

U.S. PATENT DOCUMENTS

| | | | | |
|---|---|---|---|---|
| 6,348,055 | B1 * | 2/2002 | Preissman ....................... | 606/94 |
| 6,676,664 | B1 * | 1/2004 | Al-Assir ......................... | 606/94 |
| 6,719,761 | B1 * | 4/2004 | Reiley et al. ................... | 606/92 |
| 7,156,824 | B2 * | 1/2007 | Rosenman ..................... | 604/113 |
| 7,731,720 | B2 * | 6/2010 | Sand et al. ..................... | 606/92 |
| 7,799,035 | B2 * | 9/2010 | Krueger et al. ................ | 606/94 |
| 7,887,543 | B2 * | 2/2011 | Sand et al. ..................... | 606/92 |

(Continued)

FOREIGN PATENT DOCUMENTS

| | | |
|---|---|---|
| WO | 2005/051212 A1 | 6/2005 |
| WO | 2006/125100 A1 | 11/2006 |
| WO | 2007/036815 A2 | 4/2007 |

*Primary Examiner* — Laura Bouchelle
(74) *Attorney, Agent, or Firm* — Clark & Brody

(57) ABSTRACT

A device for injecting a viscous fluid into the body includes a tubular structure defining an inner bore for passage of the viscous fluid and a pushing piston (21) engaged in the inner bore. The tubular structure is a single-piece metal tubular body (3) extending from the first end (4) to a second end (5) provided with a connector (7) for sealable fastening of a trans-tissue injection vector. The pushing piston (21) has a metal rod (22) having a straight transverse section that is constant over its entire length and complementary, while allowing for operational clearance, with that of the bore of the metal tubular body (3).

10 Claims, 2 Drawing Sheets

(56) References Cited

U.S. PATENT DOCUMENTS

| | | |
|---|---|---|
| 7,909,833 B2 * | 3/2011 | Voellmicke ............... 606/94 |
| 7,922,690 B2 * | 4/2011 | Plishka et al. ............... 1/1 |
| 2002/0082605 A1 * | 6/2002 | Reiley et al. ............... 606/93 |
| 2002/0120240 A1 * | 8/2002 | Bagga et al. ............... 604/264 |
| 2004/0024409 A1 * | 2/2004 | Sand et al. ............... 606/92 |
| 2004/0199115 A1 * | 10/2004 | Rosenman ............... 604/113 |
| 2005/0070912 A1 | 3/2005 | Voellmicke |
| 2005/0070915 A1 * | 3/2005 | Mazzuca et al. ............... 606/93 |
| 2006/0264964 A1 * | 11/2006 | Scifert et al. ............... 606/92 |
| 2007/0055279 A1 * | 3/2007 | Sand et al. ............... 606/92 |
| 2007/0142842 A1 * | 6/2007 | Krueger et al. ............... 606/92 |
| 2007/0198023 A1 * | 8/2007 | Sand et al. ............... 606/92 |
| 2008/0065083 A1 | 3/2008 | Truckai et al. |
| 2009/0012568 A1 * | 1/2009 | Farr et al. ............... 606/279 |
| 2009/0125031 A1 * | 5/2009 | Melsheimer et al. ............... 606/94 |
| 2009/0131886 A1 * | 5/2009 | Liu et al. ............... 604/272 |
| 2009/0131950 A1 * | 5/2009 | Liu et al. ............... 606/94 |
| 2009/0149878 A1 * | 6/2009 | Truckai et al. ............... 606/186 |
| 2009/0157085 A1 * | 6/2009 | Melsheimer ............... 606/93 |
| 2009/0292289 A9 * | 11/2009 | Sand et al. ............... 606/92 |
| 2010/0217235 A1 * | 8/2010 | Thorstenson et al. ............... 604/527 |

* cited by examiner

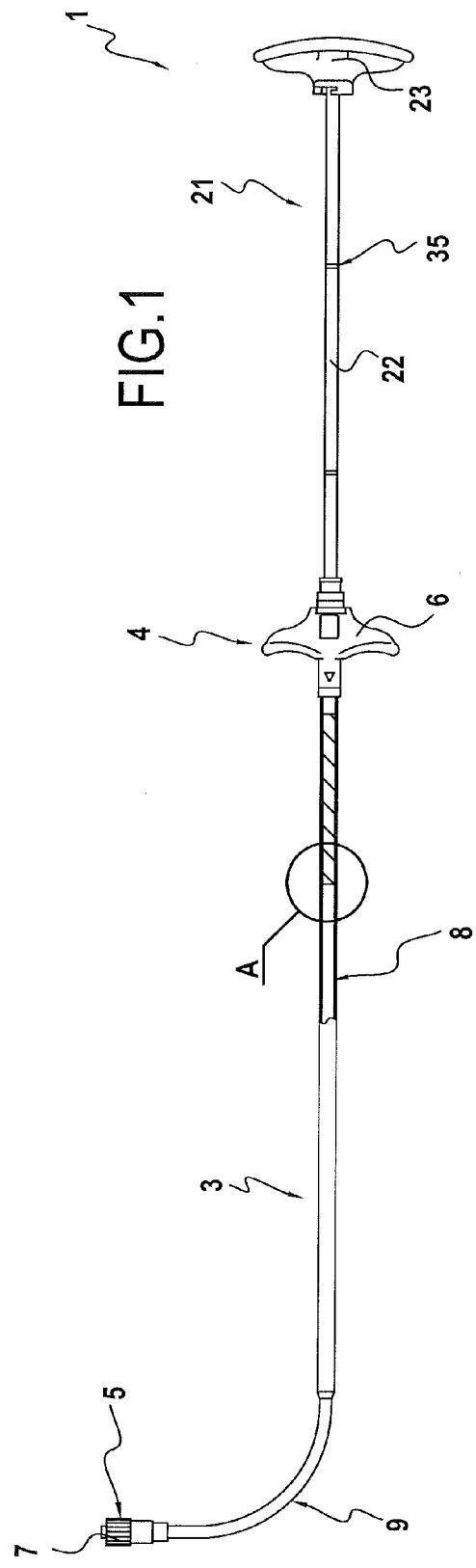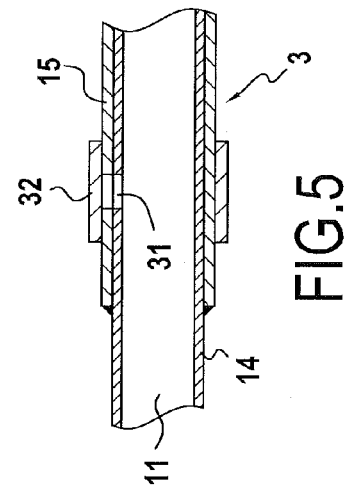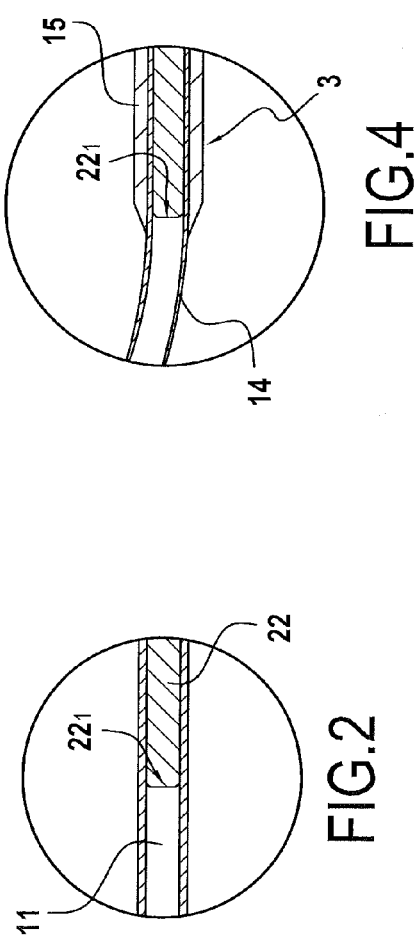

DEVICE FOR INJECTING A VISCOUS FLUID INTO THE BODY

The invention concerns the field of medical instruments, and more particularly a device adapted to ensure the high-pressure injection of a viscous fluid into the body.

The object of the invention applies to the field of surgery by injection and placement, in the form of a viscous fluid, of treatment, consolidation or prosthetic products.

As a non-limiting example, the injected viscous fluid can be of a nature to ensure bone reconstruction, in particular of the spine, by injecting bone substitutes or bone cements.

In the technical field of bone reconstruction, it is known to inject a dose of a viscous product using a syringe that is intended to be fastened to the end of an injection vector such as a trocar installed beforehand in the patient's body.

For example, patent application WO 2006/125100 describes a syringe for injecting a viscous bone reconstruction fluid including a rigid syringe body provided at one end with a gripping member and on the opposite end, with a flexible extender mounted using a connector. This syringe includes a piston rod having a straight transverse cross-shaped section. One end of the piston rod is provided with a pushing member while the opposite end engaged in the syringe body is equipped with a sealing ring.

In the field of use of this syringe, it should be considered that the injected fluid generally has a relatively significant viscosity and a significant polymerization speed. It follows that the injection operation is relatively difficult to see through and must be done quickly. In fact, the practitioner must exert relatively significant pressure on the piston of the syringe to ensure the injection of the fluid into the body. The significant thrust effort prevents the practitioner from being able to optimally control the injection procedure for the viscous fluid. Furthermore, a blockage or even deterioration of the syringe frequently occurs during the injection operation.

The object of the invention therefore aims to resolve the drawbacks of the state of the art by proposing a new device making it possible to easily ensure the high-pressure injection of a viscous fluid into a body.

Another object of the invention is to propose a device for injecting a viscous fluid, offering the possibility of occupying various positions in relation to the injection vector, to take bulk constraints around the injection site into account.

To achieve such an aim, the device for injecting a viscous fluid into the body includes:
- a tubular structure defining an inner bore for the passage of the viscous fluid, including, from a first end equipped with a gripping member, a rigid portion adjacent to a flexible portion,
- a pushing piston engaged in the inner bore, and equipped at a first end with a pushing member and having a length smaller than the length of the rigid portion.

According to the invention:
- the tubular structure is a single-piece metal tubular body extending from the first end to a second end provided with a connector for sealably fastening a trans-tissue injection vector,
- the pushing piston includes a metal rod having a transverse straight section that is constant on the entire length thereof, and complementary, while allowing for operational clearance, with that of the bore of the metal tubular body, the metal rod having, at its second end, a planar transverse face for pushing the viscous fluid.

Another object of the invention is to propose an injection device enabling precise mastery of the volume of the viscous fluid to be injected.

To that end, the injection device includes a metal rod including volume indicators for the injected fluid.

Advantageously, the metal rod has a planar transverse pushing face with a surface between 0.5 and 80 mm$^2$ and for example in the vicinity of 10 mm$^2$.

Preferably, the metal tubular body includes a flexible portion whereof the inner diameter is greater by no more than 30% than the inner diameter of the trans-tissue injection vector.

Advantageously, the metal tubular body has an essentially constant inner diameter over its entire length.

According to one alternative embodiment, the tubular body includes a rigid tube capable of forming the rigid portion of the tubular body, the rigid tube being fastened around a flexible lining whereof one portion extends outside the rigid tube so as to form the flexible portion of the metal tubular body.

According to another alternative embodiment, the tubular body includes a flexible tube on the end of which a rigid tube is fitted whereof the inner diameter determines the volume of fluid injected.

According to another alternative embodiment, the tubular body includes an orifice provided with a safety member.

Advantageously, the safety member is mounted mobile to release the orifice in order to purge the tubular body.

Preferably, the tubular body has a straight rigid portion and a curved flexible portion.

According to one feature of the invention, the injection device includes a tubular jacket concentrically surrounding the metal tubular body over at least part of its length to define, with the metal tubular body, a sealed cooling enclosure, communicating with a coolant inlet and a coolant outlet.

Various other features will emerge from the description below in reference to the appended drawings, which show, as non-limiting examples, embodiments of the object of the invention.

FIG. 1 is a partial cross-sectional view of an injection device according to the invention, in the beginning of pushing.

FIG. 2 is a view of detail "A" of the injection device shown in FIG. 1.

FIG. 4 is a view of detail "B" of the device illustrated in FIG. 3.

FIG. 5 is a partial cross-sectional view showing a characteristic detail of another alternative embodiment of the injection device according to the invention.

Figure 3:
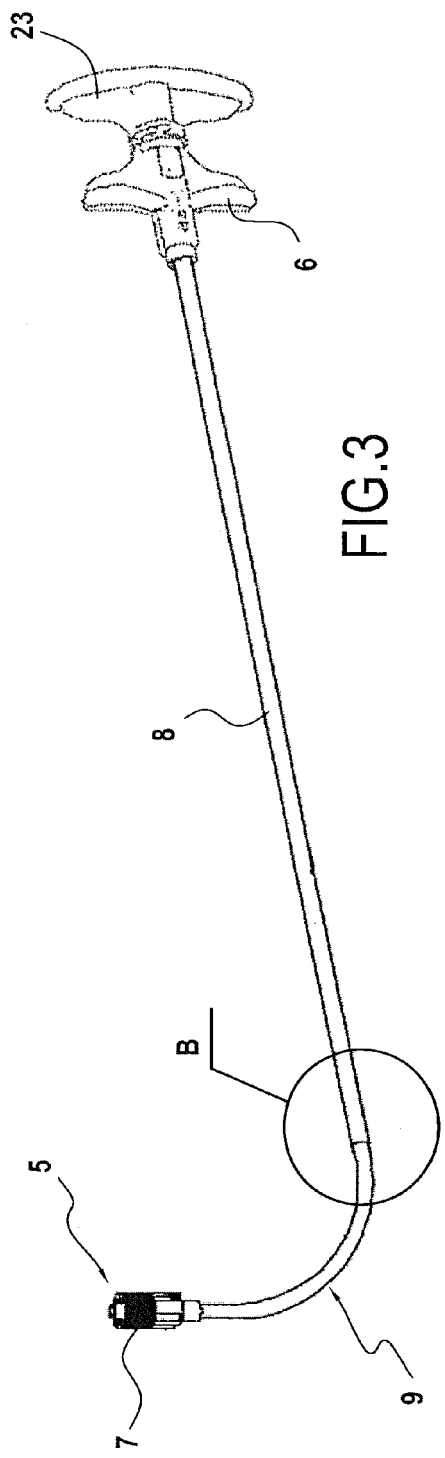
FIG. 3 is a perspective view of the injection device at the end of pushing.

As emerges more precisely from FIGS. 1 to 4, the object of the invention concerns a device 1 making it possible to ensure the injection into the body of a viscous fluid in the general meaning. As an example, the device 1 allows the injection as viscous fluid, of bone substitutes, bone cements or any intra-tissue filling material.

The injection device 1 includes a metal tubular body 3 including a first end 4 and a second end 5 opposite the first. The first end 4 is provided with a gripping member 6 attached on the tubular body 3, which can be made of a plastic material. As an example, the gripping member 6 has two branches extending on either side of the metal tubular body 3 to allow bearing on its front face of the operator's fingers. The second end 5 of the tubular body 3 is provided with a connector 7 allowing the sealed fastening of a trans-tissue vector of any type known in itself such as a trocar or similar. The connector 7 is made of any suitable material and can include a rotary collar provided with an inner threading to ensure the temporary assembly with the injection vector.

The metal tubular body 3 includes, from the first end, a rigid portion 8 and from the second end 5, a flexible portion 9 that connects to the rigid portion 8. In other words, the rigid portion 8 and the flexible portion 9 are adjacent to form the metal tubular body 3 together. It must be considered that the tubular body 3 is a single piece or continuous with the first end 4 at the second end 5. The tubular body 3 therefore does not have a connector between the rigid portion 8 and the flexible portion 9, like the tubular structure of a syringe including a rigid body on which a flexible extender is removably mounted can have. The rigid portion 8 and the flexible portion 9 are connected together permanently or without connector to form a single piece.

The tubular body 3 inwardly defines a channel, a housing or an inner bore 11, for passage of the viscous fluid from the first end 4 to the second end 5.

According to a first preferred alternative of the invention, the inner bore 11 of the metal tubular body 3 has a diameter that is essentially constant over its entire length. For example, the metal tubular body 3 and the bore 11 have a straight circular transverse section. For example, the bore 11 of the tubular body has a diameter between 0.5 mm and 10 mm and preferably in the vicinity of 3 mm.

In the illustrated embodiment shown in FIG. 4, the metal tubular body 3 includes a flexible metal lining 14 extending from one end to the other of the tubular body 3 while defining the inner bore 11 of the tubular body. A rigid metal tube 15 is fastened using any suitable means on a portion of the flexible lining 14 so as to form the rigid portion 8 of the metal tubular body 3. Thus, a portion of the flexible lining 14 extends outside the rigid tube 15 so as to form the flexible portion 9. Advantageously, the rigid portion 8 of the tubular body 3 is straight while the flexible portion 9 is curved or rounded such that the end 7 of the metal tubular body 3 extends along a direction essentially perpendicular to the direction of extension of the rigid portion 8. Of course, the flexible portion 9 can be deformed so as to give an angulation different from that of 90□ shown in the drawings. For example, the flexible metal lining 14 and the rigid metal tube 15 are made of stainless steel of suitable quality.

The injection device 1 also includes a pushing piston 21 designed to be engaged in the tubular metal body 3 in order to ensure the pushing of a dose of viscous fluid. The pushing piston 21 includes a metal rod 22 provided at a first end with a pushing member 23 assuming the form of a handle with two branches extending on either side of the metal rod. According to one preferred alternative embodiment, the gripping member 6 and the pushing member 23 include complementary assembly means so as to ensure, at the end of travel of the pushing piston 21, locking of the pushing piston in relation to the metal tubular body 3. In other words, these locking means make it possible, at the end of pushing travel, to ensure locking of the pushing piston 21 in relation to the body 3 for example through a relative rotational movement between the pushing piston 21 and the tubular body 3.

Advantageously, the metal rod 22 has a straight transverse section constant over its entire length and complementary to that of the housing 11 of the metal tubular body 3. The straight transverse section of the metal rod 22 is equal, while allowing for operational clearance, to the straight transverse section of the inner bore 11. In the example of the illustrated embodiment, the straight transverse sections of the metal rod 22 and of the inner bore 11 are circular, of the same value, while allowing for operational clearance. In other words, the diameter of the metal rod 22 is equal, while allowing for operational clearance, to the diameter of the bore 11 of the tubular body 3 in which the rod slides. According to one feature of the invention, the metal rod 22 is solid over its entire length, as appears clearly in the drawings.

The metal rod 22 has a length smaller than the length of the rigid portion 8 of the tubular metal body. The metal rod 22 has, at its second end opposite the first end, a planar and solid transverse face $22_1$ to ensure the pushing for the viscous fluid. In other words, the viscous fluid is pushed directly by the planar transverse end face $22_1$ of the metal rod 22. Advantageously, the metal rod 22 includes a planar transverse pushing face whereof the surface is between 0.2 and 80 mm$^2$ and preferably in the vicinity of 10 mm$^2$. For example, the metal rod 22 has a length between 5 cm and 50 cm and is made of stainless steel of appropriate quality.

It should be noted that the metal tubular body 3 is adapted to contain a dose of viscous fluid to be injected, for example, around 2.5 cm$^3$. In this respect, the ratio between the length and the diameter of the metal rod 22 is adapted to reduce the injection force while allowing the injection of a dose of viscous fluid in a single pushing operation.

According to another advantageous feature, the metal tubular body 3 includes a flexible portion 9 whereof the inner bore 11 has an inner diameter no more than 30% larger than the inner diameter of the trans-tissue injection vector. In other words, the flexible portion 9 has, at its second end, an inner diameter no more than 30% larger than the inner diameter of the trans-tissue injection vector so as to reduce the phenomena of resistance to the flow of the viscous fluid.

In the illustrated example, the rigid tube 15 is fastened around a flexible lining 14 extending over the entire length of a rigid tube 15. Of course, an alternative embodiment can be considered in which the single-piece metal tubular body 3 is made by the end-to-end assembly of the rigid tube 15 and the flexible lining 14. The assembly of the rigid tube 15 and of the flexible lining 14 is done so as to obtain a non-disassemblable single-piece tubular body, as explained above. It should be noted that according to this embodiment, the flexible lining 14 does not extend over the entire length of the rigid tube 15. The rigid tube 15 thus defines, through its inner diameter, the volume of the viscous fluid to be injected. According to this alternative embodiment, the inner diameter of the rigid tube 15 can be slightly larger than the inner diameter of the flexible portion 9 so as to define a corresponding volume of the dose of viscous fluid to be injected.

It emerges from the preceding description that the tubular body 3 and the pushing piston 21 are made of a metal material making it possible to grant the device a rigidity or a resistance to high pressure and an absence of reaction with regard to the injected viscous fluid. Moreover, the device is dimensioned so as to reduce the force to be exerted for the injection while having a limited bulk and being geometrically adapted in relation to the orientation of the injection vector. Moreover, realizing the injection device in elongated form makes it possible to carry the pushing action away in relation to the injection vector near which various equipment is installed, such as visualization or imaging systems, in particular generating ionizing radiations. Lastly, the device makes it possible to considerably increase the time during which the fluid can be injected before its polymerization.

FIG. 5 illustrates another alternative embodiment of an injection device 1 according to the invention. According to this embodiment, the tubular body includes an orifice 31 provided with a safety member 32 that is adapted to free the orifice 31 when the pressure inside the tubular body 3 reaches a determined value. Preferably, the orifice 31 is arranged on the rigid portion 8 near the flexible portion 9.

According to one preferred alternative embodiment, this safety member 32, which acts as a safety or overpressure valve, is made in the form of a deformable sleeve mounted on the tubular body 3 while closing the orifice 31. When an overpressure occurs inside the body 3, the sleeve 32 deforms to allow the orifice 31 to open to vent the body 3. According to one alternative embodiment, the sleeve 32 is movably mounted in translation on the tubular body 3 so as to make it possible to release the orifice 31 in order to purge the tubular body. Thus, it can be possible to release the pushing rod 22 from the tubular body so as to introduce, into the body 3, a dose of viscous fluid designed to be pushed by said rod 22 in order to complete the injected dose.

According to one preferred alternative embodiment, the metal rod 22 includes indicators 35 of the volume of injected fluid, done for example through graduations arranged on the metal rod 22.

Figure 6:
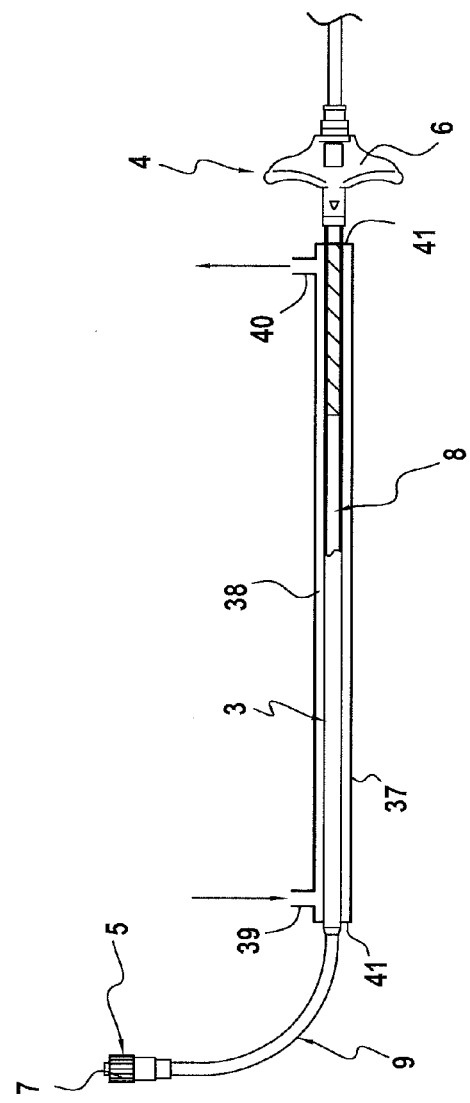
FIG. 6 is a partial cross-sectional illustration showing an alternative embodiment of the injection device according to the invention.

FIG. 6 illustrates another alternative embodiment of the injection device according to the invention aiming to control the temperature of the viscous fluid and then its polymerization speed. According to this alternative embodiment, the injection device 1 includes a tubular jacket 37 remotely surrounding the metal tubular body 3 over at least part of its length to define, with the tubular body 3, an enclosure 38 containing a coolant. This enclosure 38 communicates with an inlet 39 and an outlet 40 for the coolant. Preferably, the tubular jacket 37 extends at most along the rigid portion 8 of the tubular body 3. This tubular jacket 37 is sealably fastened on the tubular body 3 using end walls 41. The inlet 39 and the outlet 40 communicate with a coolant circulation circuit. Such a circulation circuit, not illustrated but known in itself, is equipped with means making it possible to control the temperature of the coolant fluid.

The invention is not limited to the examples disclosed and illustrated, as various modifications can be made to it without going beyond its scope.

The invention claimed is:

1. A device for injecting a viscous fluid into the body, comprising:
    a tubular structure including a first end (4) and a second end (5) opposite the first end, a gripping member (6) being attached at the first end (4) of the tubular structure and the second end (5) being provided with a connector (7) for sealable fastening of a trans-tissue injection vector, the tubular structure defining an inner bore (11) for passage of the viscous fluid, the tubular structure including from the first end (4), a rigid portion (8), and from the second end (5), a flexible portion (9) that connects to the rigid portion (8),
    a pushing piston (21) engaged in the inner bore (11), and comprising a first end and a second end opposite the first end, the first end of the pushing piston equipped with a pushing member (23), the pushing piston having a length smaller than the length of the rigid portion (8), characterized in that:
    the tubular structure is a metal tubular body (3) including the rigid portion (8) and the flexible portion (9) connected together permanently and extending from the first end (4) of the tubular structure to the second end (5) of the tubular structure, the inner bore (11) of the metal tubular body (3) having a diameter that is essentially constant between the first end and the second end of the metal tubular body (3),
    the pushing piston (21) has a metal rod (22) having a straight transverse section that is constant over its entire length between first and second ends thereof, the diameter of the metal rod (22), while allowing for operational clearance, is equal to the diameter of the inner bore (11) of the metal tubular body (3), the metal rod (22) having, at the second end thereof, a planar transverse face ($22_1$) for pushing the viscous fluid,
    wherein the rigid portion (8) is straight.

2. The injection device according to claim 1, characterized in that the metal rod (22) includes indicators (35) of the volume of injected fluid.

3. The injection device according to claim 1, characterized in that the metal rod (22) includes a planar transverse pushing face with a surface between 0.5 and 80 mm$^2$.

4. The injection device according to claim 3, wherein the surface of the planar transverse pushing face is in the vicinity of 10 mm$^2$.

5. The injection device according to claim 1, characterized in that an inner diameter of the flexible portion (9) is no more than 30% larger than an inner diameter of the trans-tissue injection vector.

6. The injection device according to claim 1, characterized in that the tubular body (3) comprises a rigid rube (15), the rigid tube (15) being fastened around a flexible lining (14) whereof one portion of the flexible lining (14) extends outside the rigid tube (15) so as to form the flexible portion (9) of the metal tubular body.

7. The injection device according to claim 1, wherein an inner diameter of the rigid tube determines the volume of the injected fluid.

8. The injection device according to claim 1, characterized in that the tubular body (3) includes an orifice (31) provided with a safety member (32).

9. The device according to claim 8, characterized in that the safety member (32) is mounted to release the orifice (31) in order to purge the tubular body.

10. The injection device according to claim 1, wherein a tubular jacket (37) concentrically surrounds the metal tubular body (3) on at least part of the length thereof to define, with the metal tubular body (3), a sealed cooling enclosure (38), communicating with an inlet (39) of a coolant and with an outlet (40) of the coolant.

* * * * *